United States Patent
Masuda (10) Patent No.: US 8,371,170 B2
(45) Date of Patent: Feb. 12, 2013

(54) METHOD AND APPARATUS FOR DIAGNOSING A DAMAGE IN A STRUCTURE

(75) Inventor: Arata Masuda, Kyoto (JP)

(73) Assignee: National University Corporation Kyoto Institute of Technology, Kyoto (JP)

( * ) Notice: Subject to any disclaimer, the term of this patent is extended or adjusted under 35 U.S.C. 154(b) by 155 days.

(21) Appl. No.: 12/866,974

(22) PCT Filed: Feb. 12, 2009

(86) PCT No.: PCT/JP2009/052311
§ 371 (c)(1),
(2), (4) Date: Aug. 10, 2010

(87) PCT Pub. No.: WO2009/101978
PCT Pub. Date: Aug. 20, 2009

(65) Prior Publication Data
US 2010/0319452 A1 Dec. 23, 2010

(30) Foreign Application Priority Data
Feb. 13, 2008 (JP) .................. 2008-032142

(51) Int. Cl.
*G01N 29/14* (2006.01)
*G01H 1/00* (2006.01)
(52) U.S. Cl. .......................... 73/587; 73/594
(58) Field of Classification Search ............ 73/583, 73/587, 594
See application file for complete search history.

(56) References Cited

U.S. PATENT DOCUMENTS

| 2008/0278319 | A1* | 11/2008 | Meiksin et al. | 340/540 |
| 2009/0009188 | A1* | 1/2009 | Gualtieri | 324/633 |
| 2009/0301197 | A1* | 12/2009 | De Smet | 73/587 |

FOREIGN PATENT DOCUMENTS

| JP | 2001-99760 | 4/2001 |
| JP | 2004-28907 | 1/2004 |
| JP | 2007-85733 | 4/2007 |

OTHER PUBLICATIONS

International Search Report issued Mar. 24, 2009 in International (PCT) Application No. PCT/JP2009/052311.
C. Liang, F.P. Sun, C.A. Rogers, "*An impedance method for dynamic analysis of active material systems*", Journal of Vibration and Acoustics, Transactions of the ASME, vol. 116, pp. 120-128, 1994.

(Continued)

*Primary Examiner* — Peter J Macchiarolo
*Assistant Examiner* — Rose M Miller
(74) *Attorney, Agent, or Firm* — Wenderoth, Lind & Ponack, LLP (57) ABSTRACT

In the diagnosis of a structure, at least one electromechanical transducer is fixed to a structure as an object of diagnosis and is driven with an alternating voltage of a constant amplitude, and a current flowing through the at least one electromechanical transducer is measured. Next, high frequency components around a driving frequency of the electromechanical transducer are separated from a signal of the current. Next, modulation information due to a damage is extracted from amplitude and/or phase demodulation of the high frequency components. Then a damage index is evaluated based on the modulation information. Thus, structural health can be diagnosed with use of at least one electromechanical transducer, without baseline data, in one measurement.

8 Claims, 8 Drawing Sheets

OTHER PUBLICATIONS

G. Park, H. Sohn, C.R. Farrar, D. J. Inman, "*Overview of piezoelectric impedance-based health monitoring and path forward*", The Shock and Vibration Digest, vol. 35, No. 6, pp. 451-463, 2003.

K.E.-A, Van Den Abeele, P.A. Johnson and A. Sutin, "*Nonlinear elastic wave spectroscopy (NEWS) techniques to discern material damage, Part I: Nonlinear wave modulation spectroscopy (NWMS)*", Res Nondestr Eval, vol. 12, pp. 17-30, 2000.

V. Zaitsev, V. Gusev, B. Castagnede and P. Sas, "*Micro-damage detection using a modulation technique based on dissipative nonlinear effects*", Proceedings of Forum Acusticum Sevilla 2002.

V. Zaitsev and P. Sas, "*Nonlinear response of a weakly damaged metal sample: a dissipative mechanism of vibro-acoustic interaction*", Journal of Vibration and Control, vol. 6, pp. 803-822, 2000.

Arata Masuda, et al., "*Nonlinear Damage Detection Based on Modulated Phase and Amplitude of Scattered Wave*" (Hado no Shinpuku Hencho to Iso Hencho ni Chakumoku shita Hi Senkei Sonsho Kenshutsu), Symposium on Evaluation and Diagnosis Koen Ronbunshu, The Japan Society of Mechanical Engineers, Nov. 27, 2005, vol. 4, p. 133-136.

Arata Masuda, et al., *Integrity Monitoring of Bolted Joints Using Nonlinear Wave Modulation* (Hi Senkei Hado Hencho o Mochiita Bolt Setsugobu no Kenzensei Monitoring), The Japan Society of Mechanical Engineers Dynamics, Measurement and Control Division Koenkai Ronbunshu, (CD-ROM), Dec. 7, 2006, vol. 2006, No. 655.

Arata Masuda et al., "*Monitoring of Crack Development Using Nonlinear Wave Modulation Technique*" (Hi Senkei Hado Hencho o Mochiita Crack Shinten no Monitoring), The Japan Society of Mechanical Engineers Dynamics, Measurement and Control Division Koenkai Ronbunshu, (CD-ROM), Dec. 7, 2006, vol. 2006, No. 629.

Arata Masuda et al., "*Monitoring of Crack Development Based on Nonlinear Piezoelectric Impedance Modulation*" (Hi Senkei Atsuden Impedance Henchoho ni yoru Kiretsu Shinten no Kanshi), The Japan Society of Mechanical Engineers Nenji Taikai Koen Ronbunshu, Aug. 2, 2008, p. 367-368.

Arata Masuda et al., "*Detection of Fatigue Cracks Using Nonlinear Piezoelectric Impedance Modulation Method*", 7th Symposium on evaluation and diagnosis (Nov. 26, 2008) together with an English translation thereof.

Patent Cooperation Treaty (PCT) International Preliminary Report on Patentability issued Sep. 16, 2010 in corresponding International Application No. PCT/JP2009/052311.

* cited by examiner

METHOD AND APPARATUS FOR DIAGNOSING A DAMAGE IN A STRUCTURE

BACKGROUND OF THE INVENTION

The invention relates to damage detection and structural health evaluation in various structures such as mechanical structures and facilities, buildings, civil engineering works, and aerospace structures.

Damage detection and structural health evaluation on a structure have been performed in various ways. For example, piezoelectric impedance-based damage detection technique is used to detect a damage created in a structure in an early stage. (For example, refer to JP-A 2007-085733, JP-A 2004-028907 and JP-A 2001-099760.) In the piezoelectric impedance-based damage detection technique, a piezoelectric element is affixed on a surface of a structure, and a change in dynamic characteristics of the structure due to a damage created in the structure is detected as a change in electrical impedance of the piezoelectric element in a supersonic range between a few tens kHz to a few hundreds kHz. The inverse of the electrical impedance (or admittance) of the piezoelectric element depends on electrostatic capacitance of the piezoelectric element and driving point mobility of the structure observed from the piezoelectric element. When a damage is created at a structural point near the affixed point of the piezoelectric element, the driving point mobility of the structure is changed largely in a range between a few tens kHz to a few hundreds kHz, so that the electrical impedance (or admittance) of the piezoelectric element is changed largely in the range according to a relationship between the dynamic characteristics of the structure and the electrical impedance (or admittance). Then, it is said that a very small damage is detected sensitively near the affixed point by measuring the electrical impedance of the piezoelectric element. An impedance analyzer or a device dedicated for measuring impedance is used for the measurement of electrical impedance.

However, in the piezoelectric impedance-based damage detection technique, an effect of a damage on high frequency waves is evaluated as a frequency response (impedance). Thus, the dynamical effect due to the damage is observed only as a time average. A damage is viewed as a static one, and for example, various nonlinear effects and interactions with the high frequency waves are neglected at the interface of the damaged area. Further, the evaluation is relative because a damage is detected as a "change" in electrical impedance of the piezoelectric element affixed to the structure before and after the structure is damaged, or a "baseline" data is necessary as a standard for the evaluation. The healthy impedance or admittance as a baseline varies largely with the structure, and it also depends on the affixed point or a size of the piezoelectric element. Therefore, the baseline cannot be predicted with a calculation or the like practically, and it has to be measured actually. This means that structural health cannot be decided with only one measurement in principle, and it is a large problem on the application or operation of the technique.

Further, a damage in an early stage often has a form of a "hidden damage" such as a closed crack or a kissing bond, and if such a damage is not detected, it might be a very great danger on safety management. However, a supersonic wave is transmitted through a damage such as a closed crack, so that it would be difficult to detect such a damage with the piezoelectric impedance-based damage detection technique.

On the other hand, nonlinear wave modulation-based damage detection technique is one of the techniques effective for detecting a "hidden damage" without baseline data in principle. (For example, refer to C. Liang, F. P. Sun, C. A. Rogers, An impedance method for dynamic analysis of active material systems, Journal of Vibration and Acoustics, Transactions of the ASME, Vol. 116, pp. 120-128, 1994; G. Park, H. Sohn, C. R. Farrar, D. J. Inman, Overview of piezoelectric impedance-based health monitoring and path forward, The Shock and Vibration Digest, Vol. 35, No. 6, pp. 451-463, 2003; K. E.-A. Van Den Abeele, P. A. Johnson and A. Sutin, Nonlinear elastic wave spectroscopy (NEWS) techniques to discern material damage, Part I: Nonlinear wave modulation spectroscopy (NWMS), Res Nondestr Eval, Vol. 12, pp. 17-30, 2000; V. Zaitsev, V. Gusev, B. Castagnede and P. Sas, Microdamage detection using a modulation technique based on dissipative nonlinear effects, Proceedings of Forum Acusticum Sevilla 2002, 2002; and V. Zaitsev and P. Sas, Nonlinear response of a weakly damaged metal sample: a dissipative mechanism of vibro-acoustic interaction, Journal of Vibration and Control, Vol. 6, pp. 803-822, 2000.) In this technique, it is noted that a damage such as a crack created in a structure, a slacked bolt, or detachment at an adhering face accompanies a change in contact state between contacting faces. Then, a change in contact state between the contacting faces due to low frequency dynamic load fluctuations is taken out as amplitude or phase modulation of high frequency waves received from an electromechanical transducer such as a piezoelectric element. If there is no damage, no modulation occurs, and this evaluation is absolute in principle. Thus, structural health can be decided by one data acquisition with nonlinear wave modulation-based damage detection technique. Further, because this technique uses a change in variations of dynamic load at low frequencies exerting a damaged site, it has an advantage that a "hidden damage" can be detected in principle.

However, for nonlinear wave modulation-based damage detection technique, at least two piezoelectric elements are needed for sending and receiving high frequency waves, and this is a problem when the technique is applied to a situation wherein a space for affixing the piezoelectric elements is restricted strictly. Therefore, it is a problem to develop a self-sensing technique using only one piezoelectric element.

SUMMARY OF THE INVENTION

Problem

An object of the invention is to detect a damage created in a structure easily in an early stage.

Solution

In a method for diagnosing a structure according to the invention, at least one electromechanical transducer is fixed to a structure as an object of diagnosis and is driven with an alternating voltage of a constant amplitude, and a current flowing through the at least one electromechanical transducer is measured. Next, high frequency components around a driving frequency of the electromechanical transducer are separated from the current signal. Next, modulation information due to a damage is extracted from amplitude and/or phase demodulation of the high frequency components, and a damage index is evaluated based on the modulation information.

A diagnosis apparatus according to the invention includes a separator for separating high frequency components around a driving frequency of an electromechanical transducer from a current signal flowing through at least one electromechanical transducer when the transducer fixed to a structure as an object of diagnosis is driven with an alternating voltage of a constant amplitude, an extractor for extracting modulation information due to a damage from amplitude and/or phase demodulation of the high frequency components, and an evaluator for evaluating a damage index based on modulation information after the amplitude demodulation and/or modulation information after the phase demodulation.

Advantages of the Invention

In the damage diagnosis according to the invention, the healthy state is not needed to be stored as baseline data, and structural health can be decided with only one measurement. Further, it can be applied to evaluate an existing structure.

Further, in the damage diagnosis according to the invention, in the smallest configuration, self sensing with use of only one electromechanical transducer can be used for evaluating a damage, and this makes it possible to provide a simpler system.

DETAILED DESCRIPTION OF THE PREFERRED EMBODIMENTS

Embodiments of the invention are described below with reference to the appended drawings.

When a piezoelectric element (probe) is affixed to a surface of a structure, a following relationship (1) holds between deformation velocity V of the piezoelectric element, force F exerted on the piezoelectric element from the structure, electric voltage V between terminals of the piezoelectric element and current I flowing through the piezoelectric element.

$$\begin{bmatrix} F(\omega) \\ I(\omega) \end{bmatrix} = \begin{bmatrix} Z_p(\omega) & -A(\omega) \\ A(\omega) & Y_p(\omega) \end{bmatrix} \begin{bmatrix} V(\omega) \\ E(\omega) \end{bmatrix} \quad (1)$$

wherein $Z_p$ is mechanical impedance when the terminals of the piezoelectric element are short-circuited, $Y_p$ is admittance when deformation of the piezoelectric element is restricted, A is a force factor, and $\omega$ is frequency. On the other hand, a following relationship (2) holds $$F(\omega) = -Z_m(\omega)V(\omega) \quad (2)$$

wherein $Z_m$ is mechanical impedance of a structure viewed from the piezoelectric element. From Equations (1) and (2), admittance between the terminals of the piezoelectric element is described in Equation (3) as follows.

$$Y(\omega) = I(\omega)/E(\omega) = Y_p(\omega) + \frac{A(\omega)^2}{Z_p(\omega) + Z_m(\omega)} \quad (3)$$

When an external load W is exerted to the structure, current I flowing through the piezoelectric element is described as follows.

$$I(\omega) = Y(\omega)E(\omega) + G(\omega)W(\omega) \quad (4)$$

wherein G is a transfer function from the external load to the current. When the piezoelectric element is driven with a sinusoidal voltage e(t), wherein t is time, of a constant amplitude E of a high frequency $\omega_p$ shown below, $$e(t) = E \cos \omega_p t \quad (5)$$

and if it is assumed that frequency of the external load W is sufficiently lower than $\omega_p$, Equation (4) is changed to a following relationship in time domain.

$$i(t) = |Y(\omega_p)|E \cos \{\omega_p t + \angle Y(\omega_p)\} + w_g(t) \quad (6)$$

wherein $w_g(t)$ is a waveform of $G(\omega)W(\omega)$ in time domain.

Now, if a damage accompanying face-to-face contact is present in the structure, the contact state is changed by the external load w(t). Because the change of the contact state changes the scattering condition of high frequency elastic waves at the interface, the mechanical impedance $Z_n$ at high frequencies varies with w(t). By taking this into account, Equation (3) at $\omega_p$ can be rewritten as follows in a situation wherein a damage is present.

$$Y(\omega_p, w(t)) = Y_p(\omega_p) + \frac{A(\omega_p)^2}{Z_p(\omega_p) + Z_m(\omega_p, w(t))} \quad (7)$$

Then, the current i(t) can be expressed in following Equation (8).

$$i(t) = |Y(\omega_p, w(t))|E \cos \{\omega_p t + \angle Y(\omega_p, w(t))\} + w_g(t) \quad (8)$$

The first term in Equation (8) can be separated with a high pass filter, and the second term can be separated with a low pass filter. The first term is a sinusoidal waveform subjected to the amplitude and phase modulation depending on w(t). From the second term, information on the external load w(t) can be obtained. The magnitude of the amplitude or phase modulation in the first term depends on the degree of damage. Therefore, the degree of damage can be decided by using a waveform obtained by amplitude demodulation and/or phase demodulation on the first term.

Various indices are proposed on the quantitative evaluation on the degree of damage based on the magnitude of modulation. One example among them is amplitude modulation index AMI according to Equation (9). The amplitude modulation index AMI is a ratio of amplitude of the waveform after the amplitude demodulation of the first term in Equation (8) to an average of the waveform after the amplitude demodulation.

$$AMI = \frac{\max a_{HF}(t) - \min a_{HF}(t)}{\max a_{HF}(t) + \min a_{HF}(t)} \quad (9)$$

wherein $a_{HF}(t)$ is instantaneous amplitude ratio calculated in Equation (10).

$$a_{HF}(t) = |i_{HF}(t)|/E \quad (10)$$

wherein $i_{HF}(t)$ is the first term in Equation (8) or high frequency components of the current, and the absolute value sign represents an amplitude envelope line. When an apparatus is diagnosed actually, for example, the amplitude modulation index AMI is compared with a threshold value, and if it exceeds the threshold value, it is decided that a damage is created in the structure.

Alternatively, as an index of diagnosis, phase modulation index PMI may be used. It is a ratio of amplitude of the waveform after the phase demodulation of the first term in Equation (8) to an average of the waveform after the phase demodulation. The phase modulation index PMI is calculated according to following Equation (11).

$$PMI = \frac{\max \theta_{HF}(t) - \min \theta_{HF}(t)}{\max \theta_{HF}(t) + \min \theta_{HF}(t)} \quad (11)$$

wherein $\theta_{HF}(t)$ is instantaneous phase difference calculated with following Equation (12), $$\theta_{HF}(t) = \angle i_{HF}(t) - \angle e(t) \quad (12)$$

wherein $i_{HF}(t)$ is the first term or high frequency components of current in Equation (8), and angle sign shows instantaneous phase angle. When an apparatus is diagnosed actually, for example, the phase modulation index AMI is compared with a threshold value, and if it exceeds the threshold value, it is decided that a damage is created in the structure.

Alternatively, a combination of a waveform $a_{HF}(t)$ after the amplitude demodulation and a waveform $\theta_{HF}(t)$ after the phase demodulation is used as an index of diagnosis. For example, a complex number $Z_{HF}(t)$ is defined according to a following equation $$z_{HF}(t) = a_{HF}(t) e^{i\omega \theta_{HF}(t)} \quad (13)$$

The complex number $Z_{HF}(t)$ is an instantaneous admittance of a piezoelectric element, and a variation from the average can be evaluated with admittance modulation index YMI according to Equation (14). YMI is used as a damage index.

$$YMI = \max \left| \frac{z_{HF}(t) - \overline{z_{HF}}}{\overline{z_{HF}}} \right| \quad (14)$$

wherein the upper bars mean a time average.

Further, other various indices can be used. For example, mobility modulation index MMI according to Equation (15) is used for evaluating magnitude of modulation of instantaneous mobility of a structure, $$MMI = \max \left| \frac{z_{HF}(t) - \overline{z_{HF}}}{\overline{z_{HF}} - Y_p(\omega_p)} \right|, \quad (15)$$

Further, dynamic stiffness modulation index KMI according to Equation (16) is provided by converting the magnitude of modulation of instantaneous mobility to magnitude of modulation of dynamic stiffness.

$$KMI = \max \left| \frac{\{z_{HF}(t) - Y_p(\omega_p)\}^{-1} - \overline{\{z_{HF}(t) - Y_p(\omega_p)\}^{-1}}}{\{z_{HF}(t) - Y_p(\omega_p)\}^{-1}} \right|. \quad (16)$$

Figure 1:
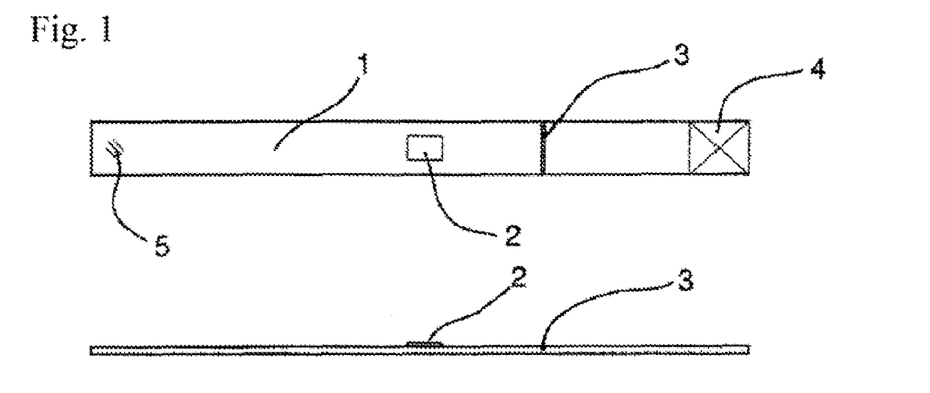
FIG. 1 is a diagram of a test specimen having a preparatory crack.

An example of a test is explained below. FIG. 1 shows a test specimen having a preparatory crack. In FIG. 1, the upper side shows a top view and the lower side shows a plan view. A preparatory crack 3 is introduced with electro-discharge machining in a beam 1 having a size of rectangular parallelepiped of 44 mm*550 mm*6 mm and made of steel material SS400 (JIS G3101). A fatigue crack is made grown from the preparatory crack 3 as a starting point by applying vibrations. For example, the preparatory crack 3 is a groove of width of 1 mm. A piezoelectric element 2 such as lead zirconate titanate (PZT) is affixed to the specimen 1. The test specimen 1 is incorporated in a structure shown in FIG. 2 at an end portion 4 fixed and at another end portion 5 supported.

Figure 2:
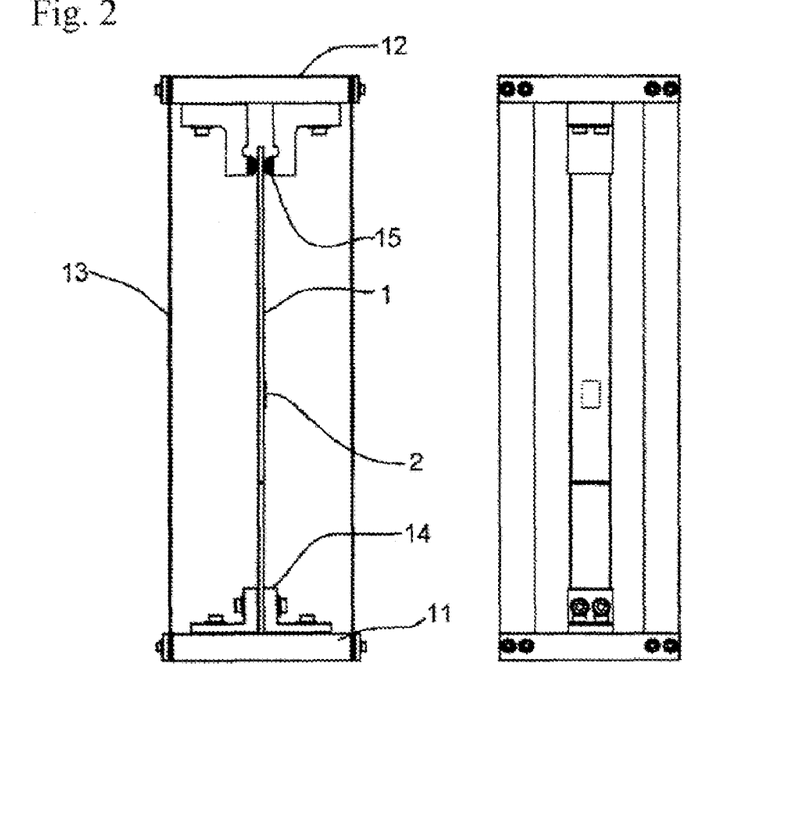
FIG. 2 is a diagram of a structure incorporating the test specimen.

FIG. 2 shows a structure incorporating the test specimen 1. In FIG. 2, the left side shows a front view and the right side shows a side view. The end portion 4 of the test specimen 1 is fixed with a bolt to a base plate 11 via a fixing jig 14. On the other hand, the portion 5 to be supported is connected to a slab 12 via a semi-cylinder made of hard rubber. The base plate 11 and the slab 12 are connected with four leaf springs 13. As a result, the structure is a vibrating system wherein the slab 12 is subjected to shear deformation relative to the base plate 11.

Figure 3:
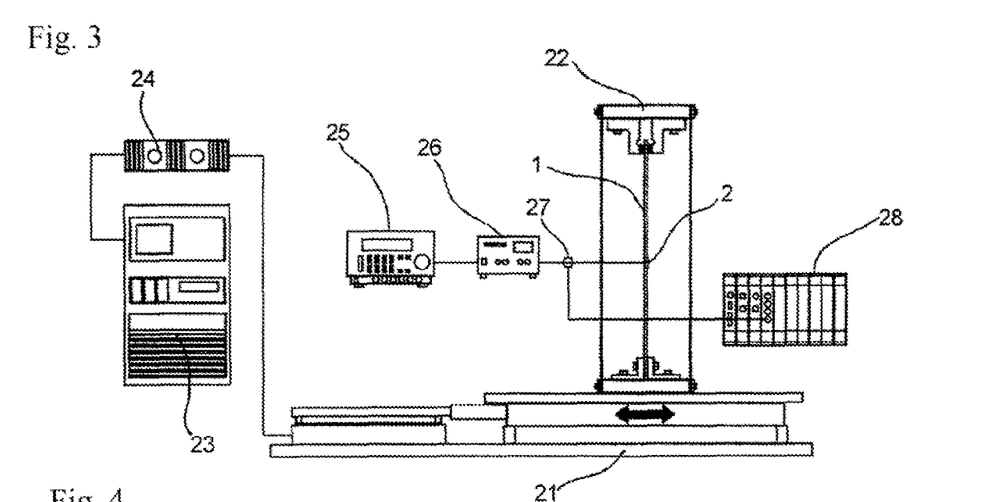
FIG. 3 is a diagram of an entire test apparatus.

FIG. 3 shows an entire test apparatus. In order to perform an experiment to grow a fatigue crack in the test specimen 1, the entire structure 22 is put on a vibrating stage 21 and is vibrated horizontally. The vibrating stage 21 is driven for sinusoidal vibrations by a controller 23 and an amplifier 24. A high frequency sinusoidal voltage is given to the piezoelectric element 2 affixed to the test specimen 1 by a signal generator 25 and an amplifier 26, while a current flowing through the piezoelectric element 2 is measured with a current detector 27. The measured data are stored in a data acquisition apparatus 28, and the obtained signals are processed by a personal computer (not shown).

An experiment is performed according to a following procedure. First, the vibrating stage 21 is oscillated for one minute horizontally at a frequency in correspondence to an eigen frequency of the structure 22 so as to grow a fatigue crack in the test specimen 1. Then, the piezoelectric element 2 is driven with a high frequency sweeping wave, while a current flowing through the piezoelectric element 2 is measured by the current detector 27. Then, the admittance of the piezoelectric element 2 is observed, and its peak frequency is adopted as $\omega_p$. Next, the vibrating stage 21 is oscillated with a sine wave of 10 Hz in order to give an external load, while a current is measured when the piezoelectric element 2 affixed to the test specimen 1 is driven with a sine wave of frequency $\omega_p$. The above-mentioned growth of crack, observation of admittance and the current measurement are performed as one set, and the above procedure is repeated until the change of equivalent stiffness ratio of the test specimen exceeds 40%.

Figure 4:
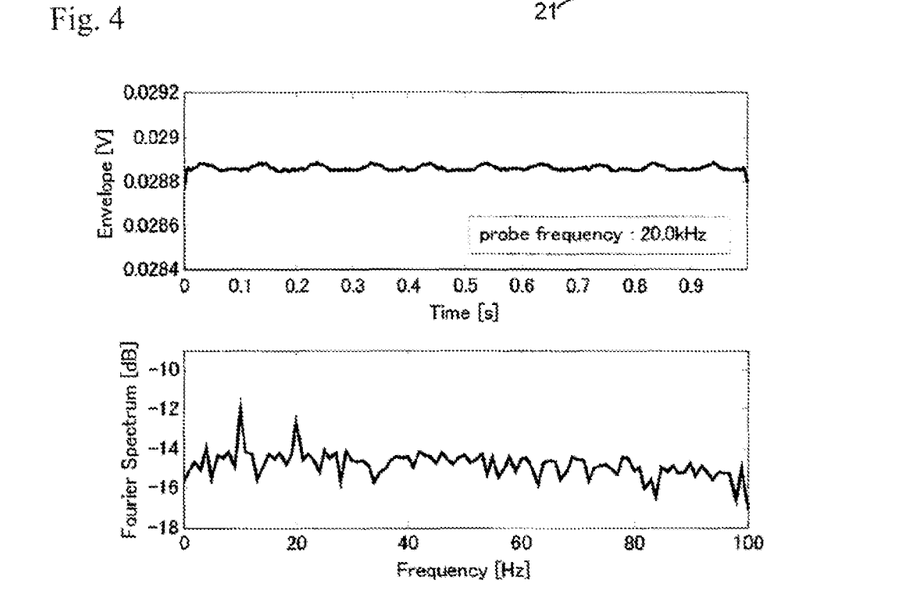
FIG. 4 is a graph of a waveform subjected to amplitude demodulation on the first term in Equation (8) in a healthy state and a Fourier spectrum thereof.
Figure 5:
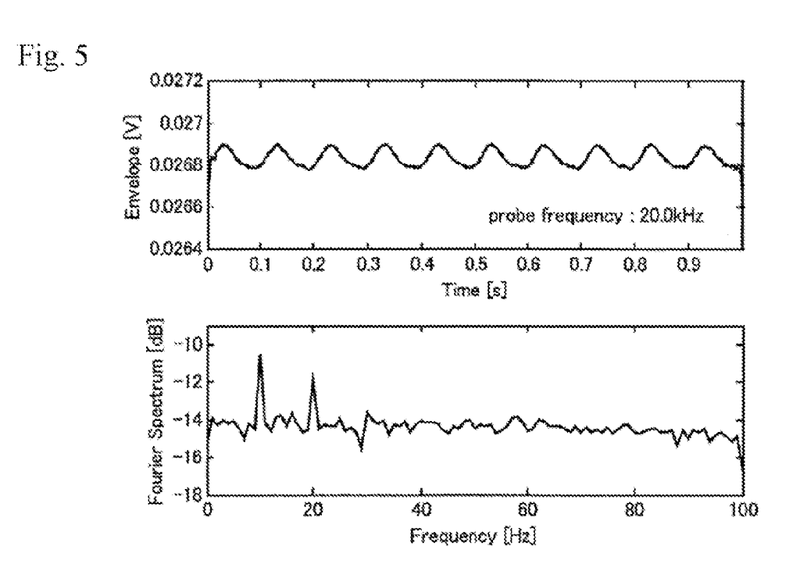
FIG. 5 is a graph of a waveform subjected to amplitude demodulation on the first term in Equation (8) in a damaged state and a Fourier spectrum thereof.

FIG. 4 show a graph of a waveform (envelope) subjected to the amplitude demodulation on the first term in Equation (8) in a healthy state plotted against time and a Fourier spectrum thereof plotted against frequency, and FIG. 5 shows a graph of a waveform (envelope) subjected to the amplitude demodulation on the first term in Equation (8) in a damaged state (5% loss in change in equivalent stiffness ratio) plotted against time and a Fourier spectrum thereof plotted against frequency. It is apparent that the amplitude modulation occurs remarkably in the damaged state.

Figure 6:
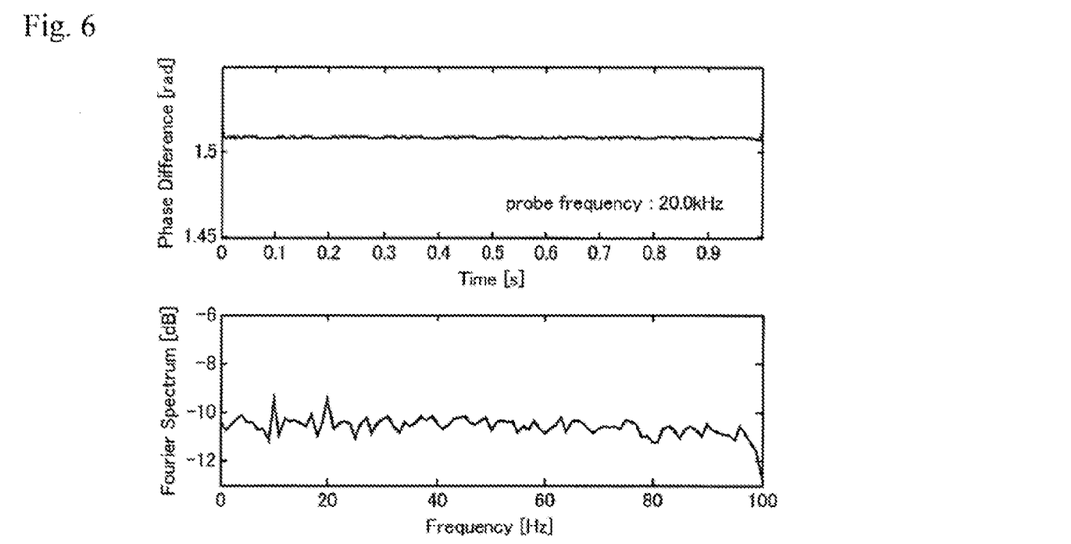
FIG. 6 is a graph of a waveform subjected to phase demodulation on the first term in Equation (8) in a healthy state and a Fourier spectrum thereof.
Figure 7:
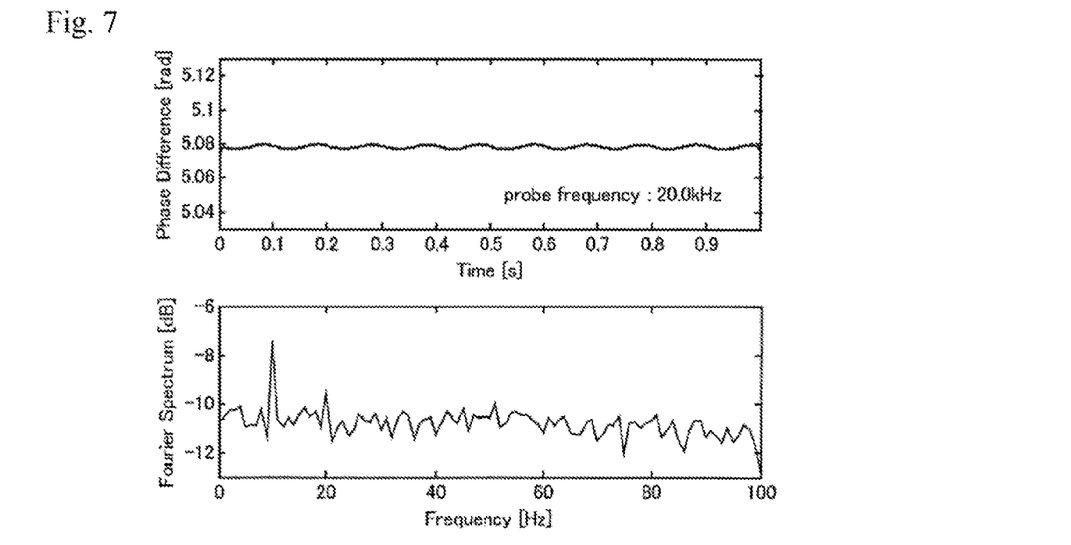
FIG. 7 is a graph of a waveform subjected to phase demodulation on the first term in Equation (8) in a damaged state and a Fourier spectrum thereof.

FIG. 6 show a graph of a waveform (phase difference) with phase demodulation on the first term in Equation (8) in a healthy state and a Fourier spectrum thereof plotted against time, and FIG. 7 shows a graph of a waveform (phase difference) with phase demodulation on the first term in Equation (8) in a damaged state (5% loss in change in equivalent stiffness ratio) plotted against time and a Fourier spectrum thereof plotted against frequency. It is apparent that the phase modulation occurs remarkably in the damaged state.

Figure 8:
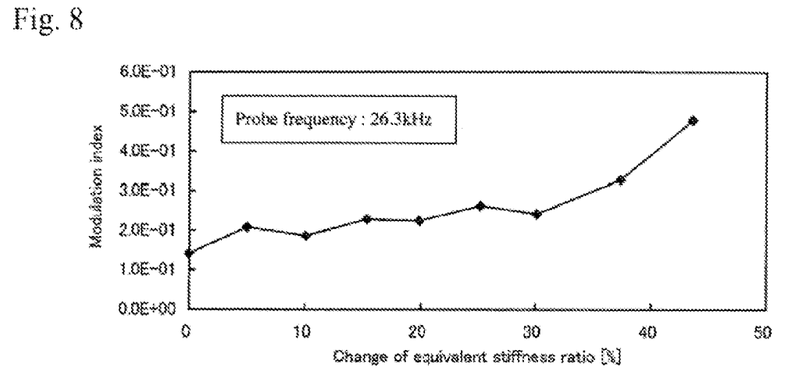
FIG. 8 is a graph of an amplitude modulation index plotted against change of equivalent stiffness ratio.

FIG. 8 is a graph of amplitude modulation index plotted against change of equivalent stiffness ratio, obtained by evaluating magnitude of the amplitude modulation with the amplitude modulation index in Equation (9).

Figure 9:
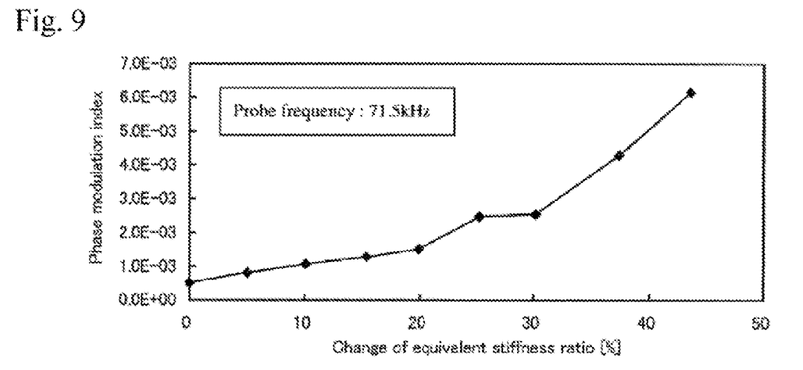
FIG. 9 is a graph of a phase modulation index plotted against change of equivalent stiffness ratio.

FIG. 9 is a graph of phase modulation index plotted against change of equivalent stiffness ratio, obtained by evaluating magnitude of the phase modulation with the phase modulation index in FIG. 11).

Figure 10:
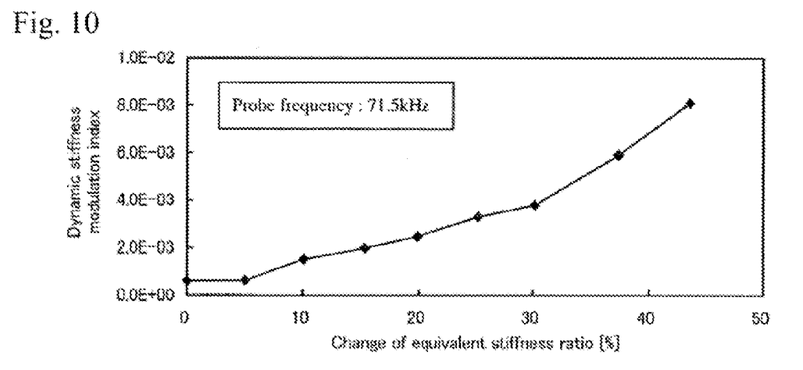
FIG. 10 is a graph of a dynamic stiffness modulation index plotted against change of equivalent stiffness ratio.

FIG. 10 is a graph of dynamic stiffness modulation index plotted against change of equivalent stiffness ratio, obtained by evaluating a damage index in Equation (16) calculated by combining a waveform after the amplitude demodulation and a waveform after the phase demodulation.

It is apparent from any of FIGS. 8, 9 and 10 that a crack in an early stage can be detected and growth of crack can be monitored, by evaluating a damage index.

Figure 11:
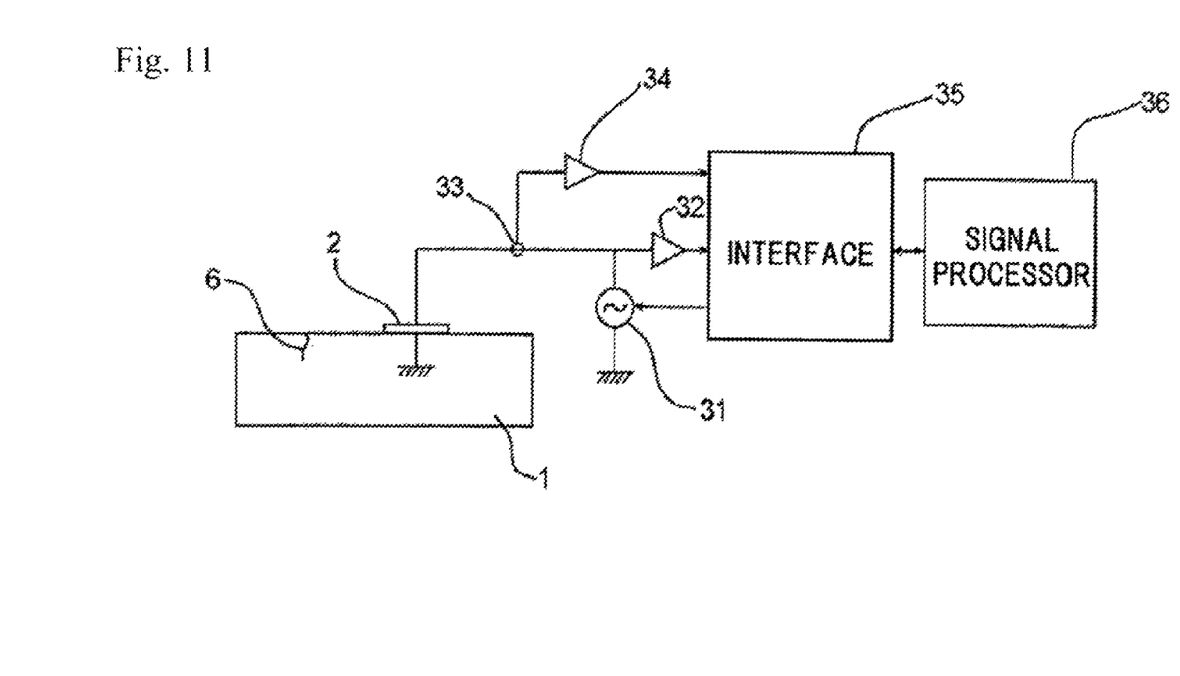
FIG. 11 is a diagram of a damage diagnosis apparatus.

FIG. 11 shows an example of a damage diagnosis apparatus. A piezoelectric element 2 affixed to a surface of a structure 1 having a damage 6 such as a crack is driven with a high frequency sinusoidal voltage by an alternating current supply 31. The driving voltage is measured with an amplifier 32. At the same time, a current flowing through the piezoelectric element 2 is measured with a current detector 33 and an amplifier 34. The voltage and current signals measured are sent via an interface 35 to a signal processor 36 for processing the signals. Waveform parameters such as the voltage amplitude, frequency and the like of the AC supply 31 are controlled through the interface 35.

Figure 12:
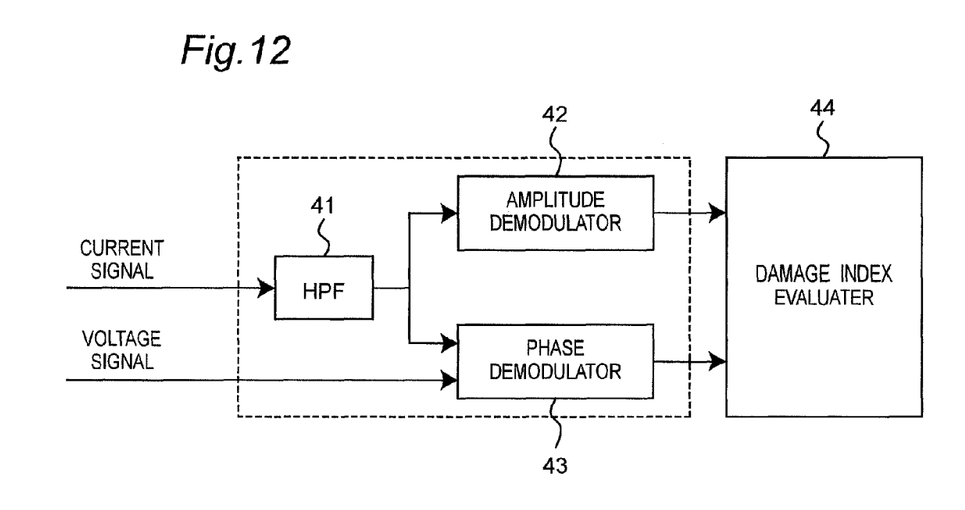
FIG. 12 is a diagram on signal processing in a signal processor.

FIG. 12 shows the contents of the signal processing in the signal processor 36. The current signal measured is divided with a high pass filter (HPF) 41 into low frequency components including information on an external load and high frequency components including information on a damage (components around the driving frequency of the piezoelectric element). The high frequency components are subjected to amplitude demodulation by the amplitude demodulator 42 and are subjected to phase demodulation by the phase demodulator 43, so as to extract demodulation information due to a damage. Next, the damage index evaluator 44 evaluates the damage index according to the low frequency components, the waveform after the amplitude demodulation and the waveform after the phase demodulation. The above-mentioned processing can be performed only with a software program, but it is desirable that components encircled with a broken line (the HPF 41, the amplitude demodulator 42 and the phase demodulator 43) are equipped as a hardware.

Figure 13:
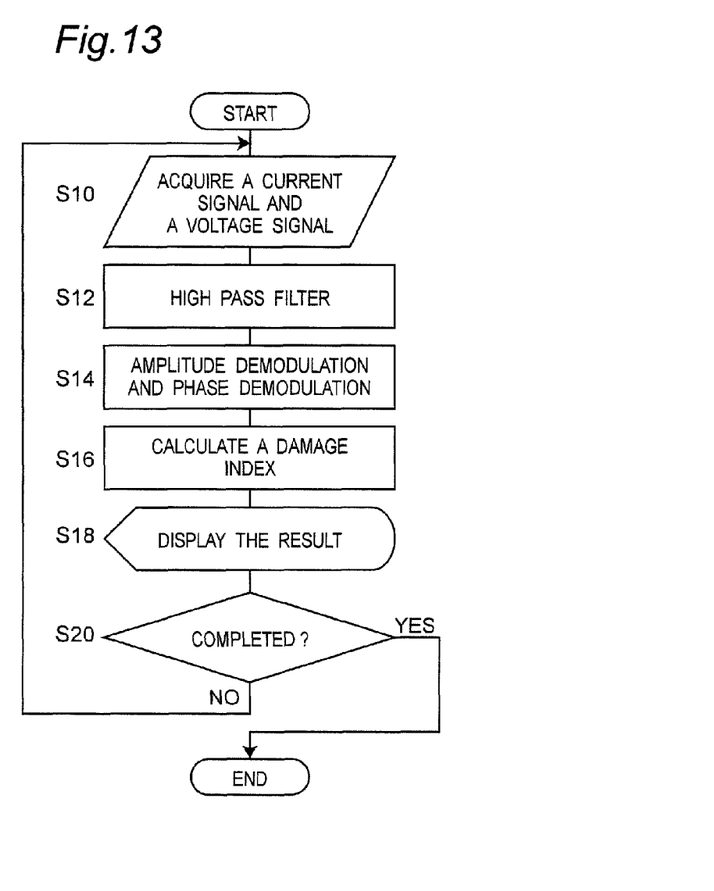
FIG. 13 is a flowchart of a software processing on signals.

FIG. 13 is a flowchart of a software processing when all the signal processing is performed by a central processing unit in the signal processor 36 with a software. First, a current signal and a voltage signal are acquired via the interface 35 from the above-mentioned measuring devices (S10). Next, the current signal is processed with the high pass filter to separate high frequency components including information on a damage (S12). Next, the separated high frequency components are subjected to amplitude demodulation, and the separated high frequency components and the voltage signal are subjected to phase demodulation (S14), to extract demodulation information due to the damage. Next, a damage index is calculated from the waveform after the amplitude demodulation and/or the waveform after the phase demodulation (S16). Then, the result is displayed (S18). If the damage index does not exceed 40% or the measurement is not completed (NO at S20), the flow returns to step S10, and the above-mentioned processes are repeated.

In the example of a damage diagnosis apparatus explained above, the piezoelectric element is used, but any electromechanical transducer other than the piezoelectric element may be used. It is also possible not to affix a transducer, but to apply a transducer as the sensor, in order to provide a portable device.

An advantage of damage diagnosis of the invention is explained below. The damage diagnosis makes use of a fact that the electrical impedance of one or more electromechanical transducers affixed to a structure shows modulation synchronous with the vibrations of the structure due to nonlinear wave modulation ascribable to nonlinearity of a damaged portion included in the structure. That is, it uses a fact that the mechanical impedance characteristic of the structure is modulated in a high frequency region in synchronization with a change in facial contact state at the damaged portion due to an external load, and the damage is measured quantitatively as modulation of a waveform of the current flowing through the piezoelectric element driven with a constant voltage amplitude at a high frequency. Because no modulation is observed for a healthy structure wherein nonlinearity due to a damage is not present, absolute evaluation of a damage is possible in principle. Because structural health is diagnosed with only one measurement, it can be applied to diagnosis for an existing structure. It is to be noted that the modulation is observed practically in a certain degree even in a healthy state, but a threshold level of the modulation can be determined reasonably beforehand for the diagnosis of structural health. On the other hand, in the prior art piezoelectric impedance-based damage detection technique, the healthy state has to be stored as a baseline data measured actually, and this was a large problem on application/operation of the technique. This is solved by the invention.

Further, in the prior art piezoelectric impedance-based damage detection technique, various nonlinear effects at the interface at the damaged portion, dynamic interaction of a load with high frequency waves, and the like are neglected. On the other hand, in the invention, by observing a current output for a voltage input precisely in time domain, various nonlinear effects such as nonlinear wave modulation can be used as useful information. Then, a "hidden damage" can be detected, and sensitivity for a very small damage is expected to be improved much.

Further, in contrast to the prior art piezoelectric impedance-based damage detection technique, the invention can be applied in principle to damage detection for a machine element such as a bearing or a gear wherein the mechanical impedance is varied dynamically.

In the prior art nonlinear wave modulation-based damage detection technique, at least two electromechanical transducers are necessary for transmission and for reception of high frequency waves. However, in the image detection according to the invention, a damage can be evaluated with self sensing in a minimum structure having only one electromechanical transducer. Thus, a simpler system can be constructed. This enhances versatility on a freedom for setting it to a structure, and this provides practical advantages. For example, it can be used easily even in a strict condition on the setting space for the device. It is also possible to provide a portable device. Further, in the minimum structure, wiring between electromechanical transducers is not necessary, and a smart element can be produced easily by integrating the electromechanical transducer with a microprocessor. Thus, a smart structure having a self diagnosis function is expected to be realized in the future.

The invention claimed is:

1. A method for diagnosing a structure comprising:
   driving at least one electromechanical transducer fixed to a structure as an object of diagnosis with an alternating voltage of a constant amplitude, and measuring a current flowing through the at least one electromechanical transducer,
   separating high frequency components around a driving frequency of the electromechanical transducer from a signal of the current,
   extracting modulation information due to a damage from amplitude demodulation of the high frequency components, and
   evaluating a damage index based on the modulation information.

2. The method according to claim 1, wherein the damage index is a ratio of amplitude of a current waveform after the demodulation to an average of the current waveform after the demodulation, and the ratio is compared with a threshold value to diagnose occurrence of a damage.

3. A diagnosis apparatus comprising:
   a separator for separating high frequency components around a driving frequency of at least one electromechanical transducer from a signal of a current flowing through the at least one electromechanical transducer when the transducer fixed to a structure as an object of diagnosis is driven with an alternating voltage of a constant amplitude,
   an extractor for extracting modulation information due to a damage from amplitude demodulation of the high frequency components, and
   an evaluator for evaluating a damage index based on the modulation information.

4. A diagnosis method comprising:
   driving at least one electromechanical transducer fixed to a structure as an object of diagnosis with an alternating voltage of a constant amplitude, and measuring a current flowing through the at least one electromechanical transducer,
   separating high frequency components around a driving frequency of the electromechanical transducer from a signal of the current,
   extracting modulation information due to a damage from phase demodulation of the high frequency components, and
   evaluating a damage index based on the modulation information.

5. The method according to claim 4, wherein the damage index is a ratio of amplitude of a current waveform after the demodulation to an average of the current waveform after the demodulation, and the ratio is compared with a threshold value to diagnose occurrence of a damage.

6. The method according to claim 4, further comprising:
   extracting the modulation information due to the damage with amplitude demodulation of the high frequency components,
   wherein the damage index is evaluated from the modulation information after the phase demodulation and the modulation information after the amplitude demodulation.

7. An diagnosis apparatus comprising:
   a separator for separating high frequency components around a driving frequency of an at least one electromechanical transducer from a signal of a current flowing through the at least one electromechanical transducer when the transducer fixed to a structure as an object of diagnosis is driven with an alternating voltage of a constant amplitude,
   an extractor for extracting modulation information due to a damage from phase demodulation of the high frequency components, and
   an evaluator for evaluating a damage index based on the modulation information.

8. The diagnosis apparatus according to claim 7, wherein the extractor further extracts modulation information due to the damage with amplitude demodulation of the high frequency components, and the evaluator evaluates the damage index from the modulation information after phase demodulation and the modulation information after amplitude demodulation.

* * * * *